United States Patent [19]

Michael

[11] Patent Number: 4,814,456

[45] Date of Patent: Mar. 21, 1989

[54] CHLORINATING WASTE STREAMS TO RECOVER CYANOPYRIDINE CONTAINED THEREIN

[75] Inventor: Herbert K. Michael, Freeport, Tex.

[73] Assignee: The Dow Chemical Company, Midland, Mich.

[21] Appl. No.: 107,716

[22] Filed: Oct. 13, 1987

Related U.S. Application Data

[63] Continuation-in-part of Ser. No. 827,855, Feb. 10, 1986, abandoned.

[51] Int. Cl.$^4$ ............................................. C07D 213/84
[52] U.S. Cl. ..................................... 546/286; 260/701
[58] Field of Search ......................... 546/286; 260/701

[56] References Cited

U.S. PATENT DOCUMENTS

| | | | |
|---|---|---|---|
| 3,317,549 | 5/1967 | Johnston | 546/286 |
| 3,420,833 | 1/1969 | Taplin, III | 546/286 |
| 3,575,992 | 4/1971 | Taplin, III | 546/286 |
| 3,591,597 | 6/1971 | Taplin, III | 546/286 |
| 3,629,424 | 12/1971 | Torba | 546/286 |
| 3,637,715 | 1/1972 | Scheidt | 546/286 |
| 3,644,380 | 2/1972 | Harmetz | 546/286 |
| 4,131,642 | 12/1978 | Miller et al. | 260/701 |
| 4,556,716 | 12/1985 | Quarroz | 546/345 |

FOREIGN PATENT DOCUMENTS 7434673 3/1974 China ................................. 546/286

OTHER PUBLICATIONS

Chem Abstracts vol. 77; 139752e (1972).

*Primary Examiner*—Mary C. Lee
*Assistant Examiner*—J. Richter
*Attorney, Agent, or Firm*—S. Preston Jones; Ronald G. Brookens

[57] ABSTRACT

Cyanopyridines are recovered from waste streams containing the same using a low temperature liquid phase chlorination step followed by filtration. This process increases recovery of unreacted cyanopyridine and significantly reduces waste stream volume.

6 Claims, No Drawings

CHLORINATING WASTE STREAMS TO RECOVER CYANOPYRIDINE CONTAINED THEREIN

CROSS-REFERENCE TO PRIOR APPLICATION

This application is a continuation-in-part of application Ser. No. 827,855 filed Feb. 10, 1986 and now abandoned.

BACKGROUND OF THE INVENTION

Many waste streams from industrial chemical plants can cause continuous waste disposal problems in addition to cost inefficiency from the loss of raw materials.

Monocyanopyridines such as 2-, 3- and 4-cyanopyridines are well known starting materials used in the preparation of various chlorinated pesticides. Such pesticides include 3-chloro-2-cyanopyridine, 4,6-dichloro-2-cyanopyridine, the isomeric dichloro-difluoro-2-cyanopyridines, the isomeric trichloro-fluoro-2-cyanopyridines, tetrachloro-2-cyanopyridine, 2,6-dichloro-3-cyanopyridine, tetrachloro-3-cyanopyridine, 2,6-dichloro-4-cyanopyridine, among others.

such compounds, their preparation by vapor phase chlorination and their uses are taught in U.S. Pat. Nos. 3,317,549: 3,420,833; 3,629,424: 3,575,992 and 3,591,597.

The 2-, 3- and 4- cyanopyridines (hereinafter called cyanopyridines) employed in the present application are normally prepared by ammoxidation of the corresponding methylpyridine ($\alpha$, $\beta$, or $\gamma$ picoline) as taught in Abramovitch "Pyridine and its Derivatives", Part 2, 1974 (page 310), U.S. Pat. No. 3,637,715, Japan Nos. 7434673 and CA 77:139752e. The product is normally only one of the isomers.

The cyanopyridine feed stream prior to its use in vapor phase chlorination processes is first dried using molecular sieves to remove excess water and other by-products including the corresponding amide. The cyanopyridine feed stream is then vaporized. The non-vaporized bottoms from this procedure and the material removed from the molecular sieve during regeneration are combined. These combined materials make up the waste stream of the present specification and claims. This waste stream is primarily composed of cyanopyridine (about 70 percent of the waste stream), water, iron, the corresponding pyridine carboxamide, dimers, trimers and tar.

Currently, the valuable cyanopyridine in the waste stream is recovered by vacuum distillation of said stream. While the waste stream is rich in cyanopyridine, its recovery is reduced since any water present tends to hydrolyze some of the cyanopyridine to the corresponding amide and the iron in the stream catalyzes further degradation. Using the vacuum distillation procedure, only about 50 percent of the cyanopyridines present in the stream are recovered. After the distillation step, the residue remaining is usually disposed of by burning.

There is a need for a more economical and efficient procedure for recovering cyanopyridines from waste streams thereby reducing the loss of this desirable material.

The present invention discloses a novel and unobvious method for recovery of approximately 85–90 percent of cyanopyridines from a waste stream by low temperature chlorination of the waste stream followed by filtration. This process increases recovery of raw materials and significantly reduces waste stream volume.

DETAILED DESCRIPTION OF THE INVENTION

The present invention is directed to a surprisingly simple method for recovering increased yields of cyanopyridine from waste streams containing the same. The waste stream is chlorinated at low temperatures which causes the solids in the stream to coagulate and precipitate without chlorination of the cyanopyridine ring structure. After chlorination, the reaction mixture is filtered to recover the cyanopyridine as the filtrate and leaving the undesirable contaminates as a water-soluble, non-filterable solid. This above method gives an increased recovery of the desired cyanopyridine and a reduction in the volume of the waste stream itself. The procedure allows for the recovery of from about 85 to 90 percent of the cyanopyridine in the waste stream.

The waste stream being treated herein is one that is created during pretreatment of the cyanopyridine feed for the vapor phase chlorination operation. The feed material is conventionally dehydrated by passing it through a standard molecular sieve bed. The treated cyanopyridine is then vaporized prior to chlorination.

The material which is removed from the molecular sieve during its regeneration constitutes one part of the waste stream and is composed essentially of cyanopyridine, pyridinecarboxyamide, water, iron and other minor contaminates.

The other part of the waste stream is composed of the non-vaporized material from the vaporization step. This material is primarily cyanopyridine, dimers, trimers and other minor contaminates.

About 70 percent of the waste stream is cyanopyridine. Currently, the waste stream is vacuum distilled wherein about 50 percent of the cyanopyridine is recovered. The residue which remains is then burned.

In the present invention, the above indicated waste stream is chlorinated, in the liquid phase, at a temperature in the range of from about 50° C. to about 80° C. In a preferred procedure for carrying out this chlorination process, the waste stream is usually mixed with a chlorinated aliphatic hydrocarbon solvent such as, for example, carbon tetrachloride, methylene chloride or perchloroethylene to produce a homogeneous solution. While it is preferred to carry out the process employing a solvent, such is not actually necessary. The presence of a solvent makes for a smoother process from an operating point of view: filtration is much more difficult without a solvent because of the excessive buildup of solids on the filter. If a solvent is not used during the chlorination step, it can be added to the reaction product prior to filtration to aid in the separation of the solids from the reaction mixture. Ideally, the waste stream is mixed with the solvent in a ratio of from about 1:1 to about 1:4 of waste stream to solvent to give adequate dilution for ease in filtration. Lower proportions of the solvent can be used as indicated above with potental filtration problems. Higher proportions of the solvent are not detrimental and raise the cost of separation because of higher materials and higher material handling cost.

The present chlorination process is normally carried out at ambient (atmospheric) pressure although increasing the pressure decreases the reaction time. The reaction is usually carried out at temperatures of from about 50° to about 90° C., preferably between about 50° to 60°

C. Lower temperatures can increase the reaction time while higher temperatures tend to reduce the solubility of the chlorine and cause adverse side reactions. The optimum reaction time is from about 10 to about 15 minutes. The end point for the chlorination reaction is marked by a phase split of the solid waste from the 2-cyanopyridine-solvent layer. The chlorine gas is delivered at a rate of between about 0.5 standard cubic feet per hour up to the saturation point of the chlorine gas in the solution.

After temperature chlorination step is complete, the reaction mixture is filtered employing conventional filtering equipment such as vacuum filter systems, Rotovac filtering systems and centrifugal filtering systems. The filtrate which comprises essentially cyanopyridine and the solvent (if one is used) is distilled to separate the cyanopyridine from the solvent, if desired. The cyanopyridine can then be returned to the vaporization step or sent directly to the vapor phase chlorination unit. If desired, prior to distillation, the filtrate can be passed through an ion exchange bed to remove any inorganic chlorides present and neutralized with a base to a pH of about 7.

The filter cake (solids) is water soluble and can be washed from the filter with water. The water-solids mixture can be further treated to further separate solids from the water or the mixture can be disposed of.

The following examples illustrate the invention but, as such, should not be construed as limiting the scope of the invention.

EXAMPLE 1

200 grams (g) of a waste stream as defined hereinabove and containing 72 percent 2-cyanopyridine, 20 percent picolinamide, 5 percent cyanopyridine trimer, ~3 percent water and 5000 ppm of iron was mixed with 668 g of carbon tetrachloride to produce a homogeneous solution. The solution, at atmospheric pressure, was heated to 60° C. with mild agitation. Gaseous chlorine was sparged through the solution at one standard cubic foot per hour (SCFH) for 10 minutes. The end of the chlorination was marked by a splitting of the waste stream into a cyanopyridine-carbon tetrachloride layer and a solids layer. The reaction mixture was cooled to 45° C. and transferred to a Buchner funnel for vacuum filtration. The product was recovered as the filtrate and was 97 percent 2-cyanopyridine, 2.5 percent picolinamide and 1500 ppm of water on a carbon tetrachloride-free basis. The recovered 2-cyanopyridine amounted to 88 percent of the 2-cyanopyridine in the waste stream. The solids (70 g) retained as a filter cake on the filter represented approximately 35 percent of the original waste stream.

Following the procedure of Example 1 using different amounts of the waste stream. The solvent was methylene chloride ($CH_2Cl_2$) or carbon tetrachloride ($CCl_4$) and the chlorine sparging time was varied. The results found are set forth below in Table I.

TABLE I

| Run | Grams Waste Stream | Grams of Solvent | Initial Temperature °C. | $Cl_2$ SCFH | $Cl_2$ Sparging Time | Grams of Solids Recovered | Filtered Solids as Percent of Original Waste |
|---|---|---|---|---|---|---|---|
| 2 | 447 | 453 ($CCl_4$) | 50 | 1 | 4 hrs. | 10.6 | 2.4 |
| 3 | 370 | 453 ($CH_2Cl_2$) | 50 | 1 | 1½ hrs. | 83.0 | 22 |
| 4 | 276 | 831 ($CH_2Cl_2$) | 50 | 1 | 1 hr. | 64.0 | 23 |
| 5 | 204 | 614 ($CH_2Cl_2$) | 50 | 1 | 25 min. | 43.0 | 21 |

In another run, 462 grams of a waste stream as defined in Example 1 at atmospheric pressure was heated to 60° C. with mild agitation. Gaseous chlorine was sparged through the material at 1 SCFH for 60 minutes. The temperature rose to 80° C. The reaction product was cooled to 45° C. and 250 g of methylene chloride was added. It was found that filtration occurred the same as if the solvent was present during chlorination.

What is claimed is:

1. A method for recovering cyanopyridines from waste streams which comprises chlorinating, at ambient pressure, said waste stream at a temperature in the range of from about 50° to about 80° C., filtering the chlorinated waste stream while in admixture with a chlorinated aliphatic hydrocarbon solvent in the ratio of from about 1:1 to about 1:4 of the waste stream to the solvent to separate the cyanopyridines as the filtrate.

2. The method as defined in claim 1 wherein the solvent is mixed with the waste stream prior to chlorination.

3. The method as defined in claim 1 wherein the solvent is mixed with the waste stream after chlorination.

4. The method as defined in claim 1 wherein the chlorinated solvent is carbon tetrachloride.

5. The method as defined in claim 1 wherein the chlorinated solvent is methylene chloride.

6. The method as defined in claim 1 wherein the chlorination takes place at a temperature in the range of from about 50° to about 60° C.

* * * * *